(12) United States Patent
Engelhard et al.

(10) Patent No.: US 7,014,643 B2
(45) Date of Patent: Mar. 21, 2006

(54) APPARATUS FOR ENDORECTAL PROSTATE BIOPSY

(75) Inventors: Karl Engelhard, Erlangen (DE); Hans-Peter Hollenbach, Eggolsheim (DE)

(73) Assignee: Siemens Aktiengesellschaft, Munich (DE)

( * ) Notice: Subject to any disclaimer, the term of this patent is extended or adjusted under 35 U.S.C. 154(b) by 314 days.

(21) Appl. No.: 10/214,289

(22) Filed: Aug. 7, 2002

(65) Prior Publication Data

US 2003/0036766 A1  Feb. 20, 2003

(30) Foreign Application Priority Data

Aug. 7, 2001  (DE) ............................... 101 38 707

(51) Int. Cl.
*A61B 19/00* (2006.01)
(52) U.S. Cl. ....................... 606/130; 600/410; 600/414; 600/417
(58) Field of Classification Search ................ 606/130; 600/410, 411, 414, 417
See application file for complete search history.

(56) References Cited

U.S. PATENT DOCUMENTS

| 4,809,694 | A | * | 3/1989 | Ferrara ........................ 606/130 |
| 5,678,549 | A | | 10/1997 | Heywang-Koebrunner et al. |
| 5,787,886 | A | * | 8/1998 | Kelly et al. .................. 600/407 |
| 5,947,964 | A | * | 9/1999 | Eggers et al. .................. 606/41 |
| 6,119,032 | A | * | 9/2000 | Martin et al. ................ 600/411 |
| 6,149,592 | A | * | 11/2000 | Yanof et al. ................. 600/427 |
| 6,195,577 | B1 | * | 2/2001 | Truwit et al. ................ 600/411 |
| 6,470,204 | B1 | * | 10/2002 | Uzgiris et al. ............... 600/411 |
| 6,493,574 | B1 | * | 12/2002 | Ehnholm et al. ............ 600/429 |
| 6,574,497 | B1 | * | 6/2003 | Pacetti ........................ 600/420 |

\* cited by examiner

*Primary Examiner*—Glenn K. Dawson
*Assistant Examiner*—Darwin Erezo
(74) *Attorney, Agent, or Firm*—Schiff Hardin LLP

(57) ABSTRACT

A device for MR-guided endorectal prostate biopsy has a biopsy guidance device connected to an MR system that is secured to the patient support table, and is alignable via the MR system for alignment and guidance of the biopsy needle into a preselectable target area. The biopsy guidance device contains MR-imaging markers and is provided with a trajectory setting mechanism at which the previously selected and calculated trajectory can be set.

5 Claims, 3 Drawing Sheets

APPARATUS FOR ENDORECTAL PROSTATE BIOPSY

BACKGROUND OF THE INVENTION

1. Field of the Invention

The present invention is directed to an apparatus for conducting an endorectal prostrate biopsy procedure, and in particular to a device for such a procedure conducted using magnetic resonance (MR) supervision.

2. Description of the Prior Art

Pathological changes of the prostate are a very common disease not only in advanced age. An increasing number of prostate patients require a prostate biopsy since, left untreated, the prostate carcinoma metastasizes into the adjoining lymph nodes and bones and becomes incurable beyond a certain extent of the disease. In addition to supplying the PSA value (prostate-specific antigen) that is determined from the blood specimen, a biopsy supplies additional information that is absolutely necessary for evaluating benefits and risks of a surgery.

Heretofore, such a biopsy has been implemented substantially "blind," under ultrasound supervision or as a multi-biopsy with up to 24 specimens. Frequently, however, pathological changes or the corresponding areas are visible only in an MR image.

A stereotactic attachment for a nuclear magnetic resonance tomography apparatus is proposed in German PS 43 25 206, but has not proven to be an improvement for endorectal prostate biopsy. German PS 43 25 206 describes an arrangement of apertured plates that is envisioned for a breast cancer biopsy, wherein the apertured plates can be moved toward and away from one another. The breast is compressed between the two plates, and the location at which a suspicious node is located is detected with appropriate imaging methods. Subsequently, a needle is applied exactly above this location and is pushed vertically downward. There is no mention of any sort of guide mechanism movable in space with which target region can be designationally approached, as is the case in prostate biopsy. The arrangement disclosed in German PS 43 25 206 accordingly, is completely unsuited for an endorectal prostate biopsy.

The same is true of an instrument guidance device for brain surgeries as proposed in U.S. Pat. No. 4,809,694. The guidance device disclosed therein allows an instrument to be swiveled in all possible directions on the basis of a ball bearing. This patent, however, does not provide any teachings as to how a specific, suspicious location is to be targeted with such an instrument in a prostate biopsy.

SUMMARY OF THE INVENTION

An object of the present invention is to provide a device for an MR-guided endorectal prostate biopsy procedure that enables an exact targeting of a suspicious target area for the removal of a biopsy specimen in a simple way.

This object is inventively achieved in a biopsy guidance device connected to an MR system that is secured to the patient support table, so as to be alignable via the MR system for alignment and guidance of the biopsy needle into a preselectable target area, and wherein the biopsy guidance device contains MR-imaging markers and is provided with a trajectory setting mechanism with which the selected and calculated trajectory can be set.

Image datasets in 2D and/or 3D of the patient can be registered wherein the physician determines the paracentesis point and target point of the biopsy. The optimum 3D biopsy trajectory and the paracentesis depth can be calculated from these points.

The biopsy guidance device can be either manually adjustable or motor-adjustable using a calculating unit coupled to the MR system.

After the alignment of the biopsy device has ensued in this way, a check of the trajectory ensues by MR imaging along the trajectory in two planes.

The technique made available with the inventive device allows a high-quality biopsy given simultaneously low cost outlay and low stress and negligible risk for the patient.

In a first embodiment of the invention, the biopsy guidance device contains a freely rotatably seated sphere having a guide channel for the biopsy needle. The sphere can have graduated circles around its poles and equator with degree divisions for setting the guidance trajectory on the basis of the measured MR image datasets.

It has proven especially expedient in an embodiment of the invention to provide trajectory monitoring cavities that can be filled with water and that proceed parallel to the guidance channel, these being visible in the MR image. During the implementation of the intervention, the trajectory thus can be tracked at any time under MR-imaging supervision.

In a second embodiment of the invention, the biopsy guidance device has a guidance block with a number of guidance channels proceeding through the block that are inclined relative to one another and correspond to possible biopsy trajectories.

The guidance channels can be numbered, and the best-suited channel is selected after the production of the MR image datasets.

In a further embodiment of the invention the biopsy guidance device contains spaced apertured grid plates for prescribing the possible biopsy trajectories. The combinations of the multiple holes in one of the plates with one of the multiple holes of the other plate yields a large number of possible trajectories along which the biopsy needle can be guided.

Fundamentally, an endorectal coil with a prostate biopsy attachment can be provided for the implementation of a biopsy procedure with the inventive device. Due to the greater freedom and the more versatile guidance possibilities, however, it has proven especially expedient to separate the biopsy device from the endorectal coil and to provide the biopsy needle with an inflatable rubber cuff or the like in the region of the needle tip for guidance thereof. The needle tip preferably is fashioned as a snap tip with an adjustable extended length. After being introduced, this simulates the endorectal coil pressed against the prostate in the prior image registration and causes to a displacement of the prostate as in the preceding fine structure exposure obtained with the endorectal coil.

DESCRIPTION OF THE PREFERRED EMBODIMENTS

Figure 1:
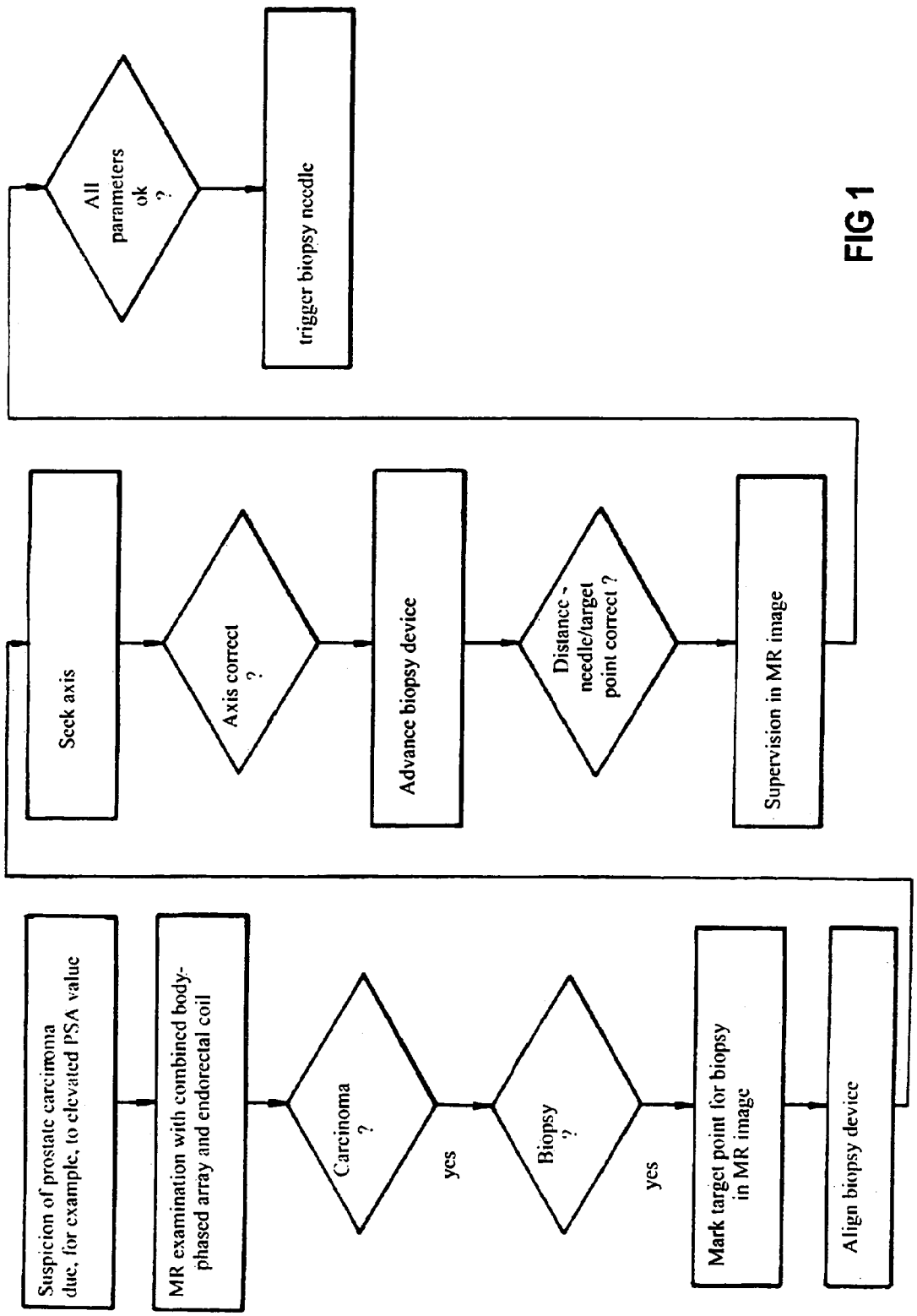
FIG. 1 is a flowchart of a prostate carcinoma examination including the inventive, MR-guided prostate biopsy.

As shown in FIG. 1, an MR examination with combined body phased array coil and endorectal coil for primary tumor recognition and for confirming or excluding the presence of a carcinoma is first implemented given a suspected prostate carcinoma, for example due to an elevated PSA value and/or other clinical findings.

If a carcinoma is not detected, then the examination is ended. If a suspected carcinoma can be recognized in the images, then a decision must be made whether a biopsy is additionally needed. If a biopsy is not necessary, the examination can be ended. Given the need for a biopsy, the location to be biopsied, i.e. the target point, is marked in the MR image and the coordinates are thus defined. Subsequently, the biopsy device (FIGS. 2 through 5) is introduced and aligned. After the exposure of a 2D or 3D dataset, the axis that the biopsy device forms with the target point, i.e. the straight line between the target point coordinates and coordinates of the biopsy device, is sought, and the biopsy device is displaced until this axis has been found. Subsequently, the biopsy device is moved as close as possible to the suspicious region. After again reviewing the axis and correction as needed under MR supervision, the biopsy needle, that is preferably fashioned as a snap tip, can be triggered.

Figure 2:
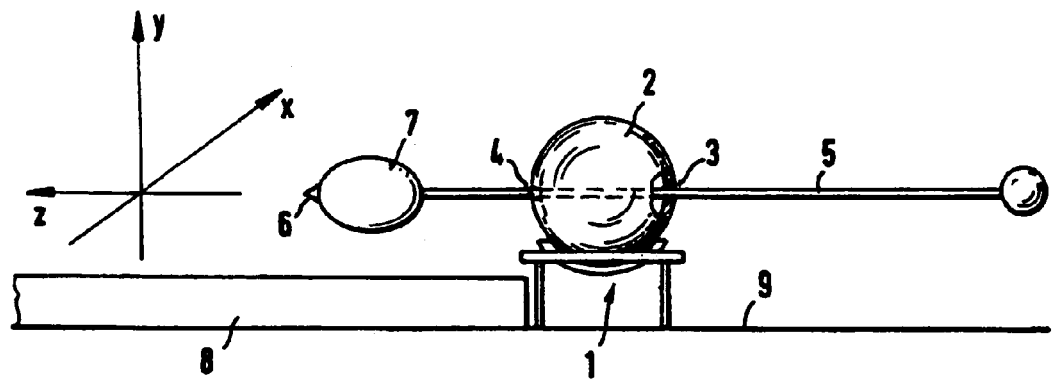
FIG. 2 is a schematic illustration of a first embodiment of an inventive prostate biopsy device in a side view.
Figure 3:
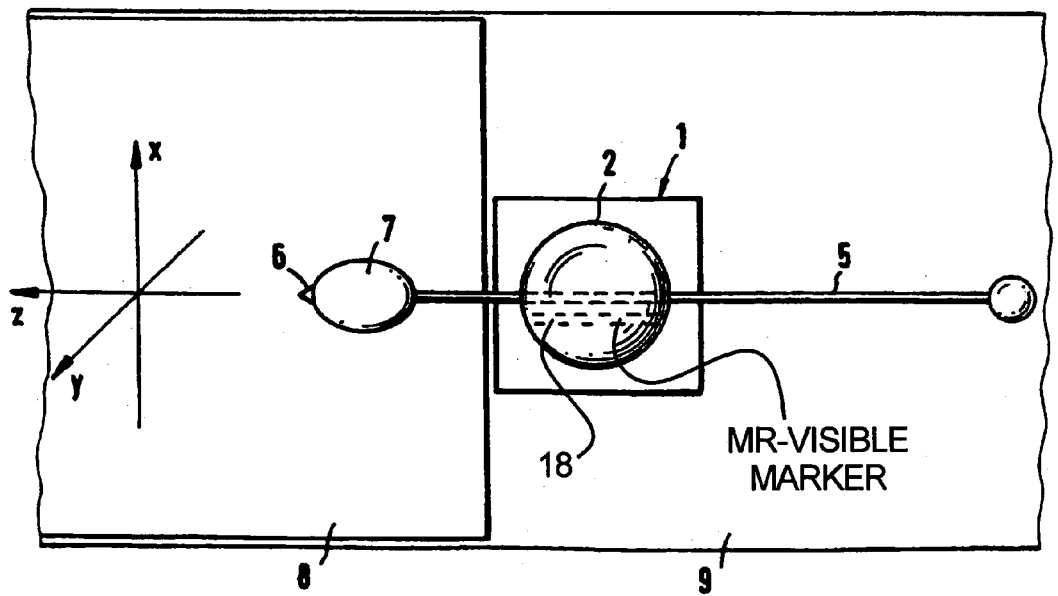
FIG. 3 is a plan view of the prostate biopsy device of FIG. 2.

A sphere 2 having bores 3 and 4 lying opposite one another for a needle guide 5, for example a tube, is seated on a mount 1 so as to be rotatable in all directions, serves for guiding the biopsy needle under MR supervision in the exemplary embodiment according to FIGS. 2 and 3. The freely rotatable sphere 2 can be provided with graduated circles with degree division for the navigation. An inflatable rubber ball or cuff 7 is provided in the region of the tip 6 of the biopsy needle, the tip 6 being fashioned as a snap tip. The inflatable rubber ball 7 is pressed against the prostate after introduction into the rectum in the same way as the endorectal coil previously utilized for the fine exposure in order to reproduce the displacement of the prostate in this previous fine structure exposure. The mount 1 for the sphere 2 is rigidly arranged on the patient table 9 in front of the cushion 8. Corresponding to the image datasets in 2D and/or 3D identified with the assistance of the endorectal coil, the positions to be approached in the different x, y and z directions can be set by suitable rotating the sphere 2.

As needed, the needle guide 5 can have an articulation with the internally displaceable biopsy needle between the tip 6 and the inflatable rubber ball 7 in order to also be able to implement a targeting with the assistance of the inventive device in the case of an unfavorably placed carcinoma.

Figure 4:
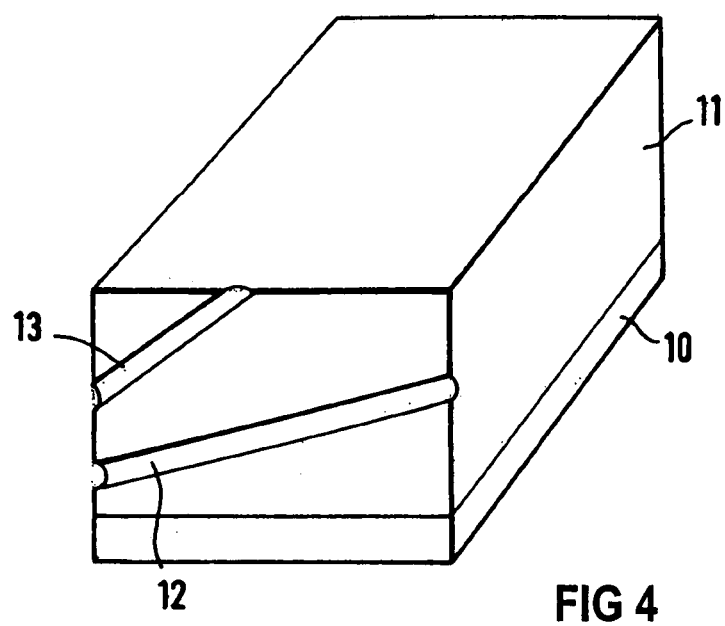
FIG. 4 illustrates a second embodiment of the inventive biopsy guidance device in the form of a block containing a number of through bores.

FIG. 4 shows a block 10 securable to the patient support table via a mount element 10 that can be utilized instead of the above-described, rotatable sphere 2. The block 11 contains numerous, numbered, through channels of which only the channels 12 and 13 are shown in FIG. 4 for clarity. The "best" channel proceeding from the previously calculated trajectory angle for targeting the identified carcinoma in the prostate is selected in order to move the biopsy guide 5 for the biopsy needle and the inflatable rubber ball 7 to the prostate in an optimum way, so that a biopsy specimen can be subsequently taken.

Figure 5:
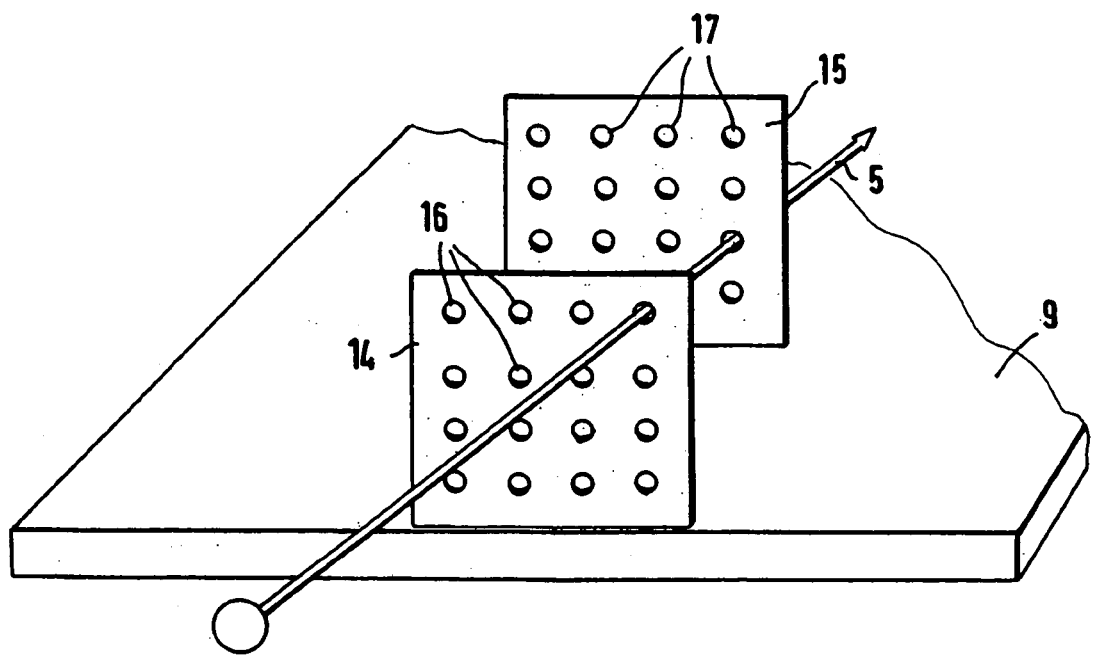
FIG. 5 illustrates a third embodiment of the inventive biopsy guidance device having spaced apertured plates.

FIG. 5 shows a further embodiment of a biopsy guidance device composed of two space apertured plates 14 and 15 that are each provided with a number of bores 16 and 17 that can be combined with one another in different ways, and thus enable a large variety of guided trajectories for the needle guide 5. Such apertured plates 14 and 15 are especially simple to manufacture and can be very easily sterilized.

The invention is not limited to the illustrated exemplary embodiments. In particular, it would thus also be possible—and this is true for all embodiments of the biopsy guidance device but preferably for those with the freely rotatable sphere 2 according to FIGS. 2 and 3—to attach elongated cavities parallel to the guidance channel that can be filled with water and that are thus visible in the MR image. One such MR visible marker 18 is shown in FIG. 3. As a result, the trajectory can be tracked at any time under MR-imaging supervision during implementation of the intervention.

Although modifications and changes may be suggested by those skilled in the art, it is the intention of the inventors to embody within the patent warranted hereon all changes and modifications as reasonably and properly come within the scope of their contribution to the art.

We claim:

1. A device for use in a magnetic resonance guided endorectal prostate biopsy procedure, comprising:
    a biopsy needle guidance device adapted for attachment to a patient support table of a magnetic resonance system;
    a magnetic resonance visible marker contained in said biopsy guidance device; and
    said biopsy guidance device having a trajectory setting mechanism adapted to receive a biopsy needle and to align and guide said biopsy needle toward a predetermined target area along a predetermined trajectory, said biopsy guidance device comprising a mount and a sphere mounted in said mount so as to be freely rotatable, said sphere having a guide channel adapted to receive said biopsy needle, and
    said sphere containing at least one cavity filled with water and proceeding parallel to said guidance channel, forming said magnetic resonance visible marker.

2. A device as claimed in claim 1 wherein said setting mechanism is manually settable.

3. A device as claimed in claim 1 wherein said setting mechanism is motor-adjustable.

4. A device as claimed in claim 1 wherein said sphere has opposite poles and plurality of graduated circles proceeding concentrically relative to said poles for use in setting said trajectory dependent on image datasets obtained with said magnetic resonance system.

5. A device as claimed in claim 1 wherein said biopsy guidance device includes a tube adapted to receive said biopsy needle, and an inflatable rubber ball disposed at a distal end of said tube which is adapted to allow a tip of said biopsy needle to project therethrough.

* * * * *